United States Patent
Heimberger

[11] Patent Number: 5,125,909
[45] Date of Patent: Jun. 30, 1992

[54] FLEXIBLE TUBULAR CHANNEL WITH EXTERNAL SUPPORTING RIDGES

[75] Inventor: Rudolf Heimberger, Oberderdingen, Fed. Rep. of Germany

[73] Assignee: Richard Wolf GmbH, Knittlingen, Fed. Rep. of Germany

[21] Appl. No.: 507,936

[22] Filed: Apr. 11, 1990

[30] Foreign Application Priority Data

Jun. 14, 1989 [DE] Fed. Rep. of Germany ....... 3919441

[51] Int. Cl.⁵ .......................................... A61M 25/00
[52] U.S. Cl. .................................. 604/264; 604/282; 138/121; 138/122
[58] Field of Search ............... 138/121, 122, 172, 173; 604/175, 264, 282, 275

[56] References Cited

U.S. PATENT DOCUMENTS

| | | | |
|---|---|---|---|
| 2,610,627 | 9/1952 | Watt et al. | 604/275 X |
| 2,747,574 | 5/1956 | De Lorenzo | 604/275 X |
| 3,618,613 | 11/1971 | Schulte | 604/282 |
| 3,738,394 | 6/1973 | Westerbarkey | 138/122 |
| 4,261,671 | 4/1981 | Langner | 405/166 |
| 4,634,432 | 1/1987 | Kocak | 604/167 |
| 4,653,542 | 3/1987 | Tascher | 138/109 |
| 4,832,681 | 5/1989 | Lenck | 600/34 |
| 4,877,354 | 10/1989 | Williamson | 405/157 |
| 4,900,314 | 2/1990 | Quackenbush | 604/282 |
| 4,950,232 | 8/1990 | Ruzicka et al. | 604/43 |
| 4,964,440 | 10/1990 | Andre et al. | 138/122 |
| 4,982,765 | 1/1991 | Usui | 138/122 |

FOREIGN PATENT DOCUMENTS 2207902 2/1989 United Kingdom ............... 604/282

Primary Examiner—John D. Yasko
Assistant Examiner—Adam J. Cermak
Attorney, Agent, or Firm—Panitch Schwarze Jacobs & Nadel

[57] ABSTRACT

A tubular channel usable in endoscopy for flexible auxiliary instruments such as forceps, electrodes and the like to be passed through, in which structuring of the outer wall face by means of a plurality of radial grooves is employed to obtain high flexibility on the one hand and on the other hand a cross-sectional strength which improves its resistance to collapse when suction is applied and also to internal pressure.

10 Claims, 1 Drawing Sheet

FLEXIBLE TUBULAR CHANNEL WITH EXTERNAL SUPPORTING RIDGES

BACKGROUND OF THE INVENTION a) Field of the Invention

The invention relates to a tubular probe channel usable in endoscopy and made from a flexible material, for flexible auxiliary instruments such as forceps, electrodes and the like to be passed through into cavities, and for feeding in and draining out irrigating liquid.

b) Description of the Prior Art

Tubular channels of this kind are a familiar part of the prior art in practice. Thus, what are normally used for the purposes quoted are highly flexible tubes of plastics material, but these do have certain disadvantages. There is for example a risk that they will collapse when suction is applied for cleaning purposes, or alternatively they may be damaged by pressures above atmospheric. What is more, there is a danger with highly flexible materials that they may be damaged when a sharp-edged and less flexible article, such as a forceps or the like, is inserted, due to the fact that articles of this kind find it difficult to follow the flexible tubular channel and apply stress to it in the lateral direction and may possibly even pierce it as they do so.

To alleviate these disadvantages, known tubular channels of this kind have been fitted with additional metal coils but this makes the channel, and particularly its distal end, more difficult to deflect.

The main object of the present invention is to design a tubular channel which on the one hand is of relatively high flexibility but on the other hand is sufficiently strong for damage of the kind described above not to occur.

SUMMARY OF THE INVENTION

To this end, the present invention consists in a tubular channel usable in endoscopy and made from a flexible material, for flexible auxiliary instruments such as forceps, electrodes and the like to be passed through, and for feeding in and draining out an irrigating liquid, characterised in that the channel is in the form of a flexible tube with a smooth inner face and in that the face of the outer wall of the tube is structured in a corrugated configuration.

The structuring can be formed by a plurality of spaced, substantially radial supporting ridges, the ratio between regions of maximum and minimum wall-thickness being approximately 2:1 and the pitch of the ridges being approximately twice the maximum wall-thickness.

This structuring makes it possible on the one hand for the desired flexibility to be obtained, because this is determined principally by the waists or in other words the areas of reduced wall-thickness, but on the other for the requisite strength to be obtained as well, because this is provided by the reinforcing effect of the respective adjoining lands or in other words areas of greater wall-thickness.

In one embodiment of the invention, the structuring of the outer peripheral surface may be produced by a plurality of substantially radial grooves, but it may equally well be obtained from at least one spiral groove.

At the same time, to avoid notch effects and for better cleanability, the groove floor may be of rounded form.

To make the tubular channel according to the invention easily insertable, the groove walls may be rounded at their transition into the outer wall face.

Finally, the strength of the tubular channel may be increased at its ends by having the depth of the grooves or groove diminish steadily in the region of at least one of the ends of the channel, thus giving the end region concerned a smooth outer face and the maximum wall-thickness for a certain length.

BRIEF DESCRIPTION OF THE DRAWINGS

In order that the invention may be more readily understood some embodiments thereof will now be described, by way of example, with reference to the accompanying drawings, in which.

DESCRIPTION OF THE PREFERRED EMBODIMENTS

Figure 1:
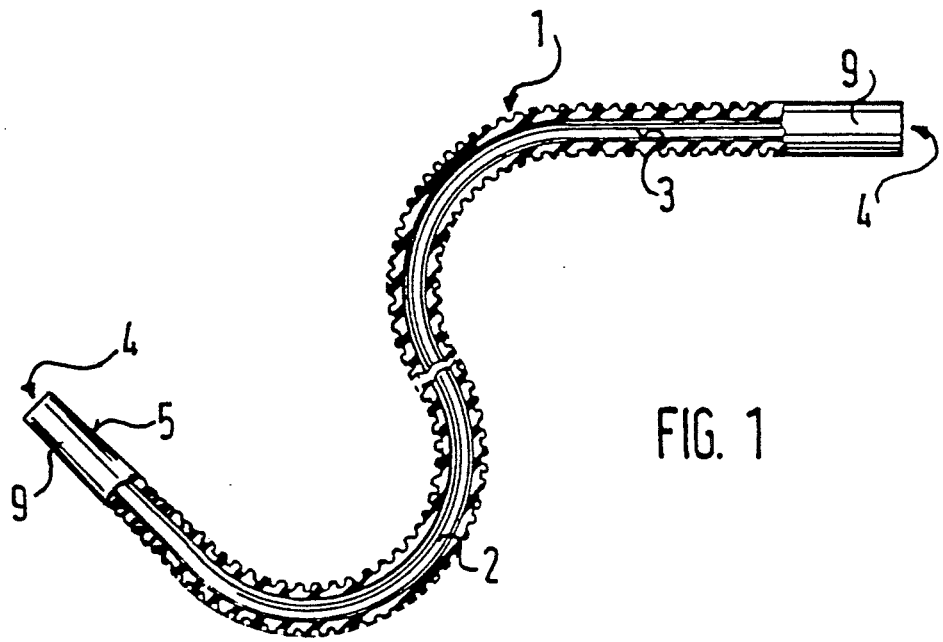
FIG. 1 shows a tubular channel constructed in accordance with the invention, shortened and partly in section, in a view which demonstrates its flexibility.

Referring to FIG. 1, there is shown a channel 1 produced in the form of a flexible tube 2, preferably from a flexible plastics material such as Teflon, (Trade Mark) which material, due to its anti-frictional properties, allows an auxiliary instrument to be inserted easily and can be cleaned without any problems. The tubular channel 1 has a smooth-faced inner wall 3 and its outer wall face, except for the two end regions 4, is structured.

Figure 2:
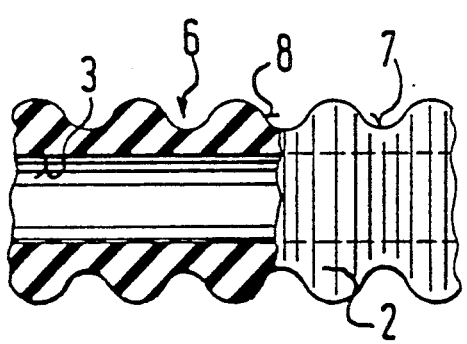
FIG. 2 shows an enlarged segment of the tubular channel in FIG. 1, partly in section.

As is best seen in FIG. 2, this structuring is produced by a plurality of radial groves 6, in the region of which the wall-thickness of the tube 2 is reduced. At the same time the floor 7 of the grooves is rounded and their walls 8 are rounded too at their transitions into the outer wall face 5. Towards the two end regions 4, the depth of the grooves 6 diminishes, thus producing unstructured end pieces 9 whose wall-thickness corresponds to the wall-thickness in the region of the lands between the grooves 6.

Figure 3:
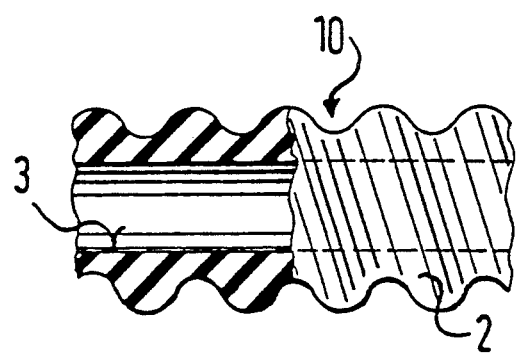
FIG. 3: Shows a segment similar to that shown in FIG. 2 of a modified embodiment.

In the embodiment shown in FIG. 3, the structuring is produced by a groove 10 which extends in a spiral, and which may also be multi-start.

Whilst particular embodiments have been described it should be appreciated that the invention includes all modifications and variations falling within its scope.

I claim:

1. A tubular probe channel comprising channel means for feeding in and draining out an irrigating liquid, said channel means having sufficient flexibility for receiving flexible auxiliary instruments, such as forceps, electrodes and the like used in endoscopy, to be passed therethrough into body cavities, said channel means being in the form of a biocompatible flexible tube having a smooth-faced inner wall and an outer wall face which is structured, the structuring being formed by a plurality of spaced, substantially radial supporting ridges, the ratio of the maximum wall thickness with ridges to the minimum wall thickness between ridges being approximately 2:1 and the ridges having a pitch of approximately twice the maximum wall thickness.

2. A tubular channel according to claim 1, wherein the structuring of the outer wall face is produced by at least one groove.

3. A tubular channel according to claim 2, wherein the at least one groove is a plurality of substantially radial grooves.

4. A tubular channel according to claim 2, wherein the at least one groove is a spiral groove.

5. A tubular channel according to claim 2 wherein the at least one groove has a floor which is of rounded form.

6. A tubular channel according to claim 2 wherein at the least one groove has walls which are rounded at their transition to the outer wall face.

7. A tubular channel according to claim 2, wherein the at least one groove has a depth which steadily diminishes in the region of at least one of two ends of the channel whereby the at least one end region has a smooth outer face for a certain length.

8. A tubular channel according to claim 1 wherein said flexible tube is of unitary construction.

9. A tubular channel according to claim 1 wherein the walls of said flexible tube are solid between said inner and outer wall faces.

10. A tubular channel according to claim 1 wherein said flexible tube is formed of a plastic material having anti-frictional properties.

* * * * *